United States Patent
Neuvonen et al.

(10) Patent No.: US 9,370,658 B2
(45) Date of Patent: Jun. 21, 2016

(54) SYSTEM AND A METHOD FOR TRANSCRANIAL STIMULATION OF A HEAD REGION OF A SUBJECT

(71) Applicant: Sooma Oy, Helsinki (FI)

(72) Inventors: Tuomas Neuvonen, Espoo (FI); Jani Virtanen, Soderkulla (FI)

(73) Assignee: Sooma Oy, Helsinki (FI)

( * ) Notice: Subject to any disclaimer, the term of this patent is extended or adjusted under 35 U.S.C. 154(b) by 0 days.

(21) Appl. No.: 14/590,917

(22) Filed: Jan. 6, 2015

(65) Prior Publication Data
US 2015/0190635 A1    Jul. 9, 2015

(30) Foreign Application Priority Data
Jan. 7, 2014   (GB) .................................. 1400250.5

(51) Int. Cl.
*A61N 1/36* (2006.01)
*A61N 1/372* (2006.01)
*A61N 1/04* (2006.01)
*A61N 1/20* (2006.01)

(52) U.S. Cl.
CPC ........... *A61N 1/36014* (2013.01); *A61N 1/0472* (2013.01); *A61N 1/0476* (2013.01); *A61N 1/205* (2013.01); *A61N 1/36021* (2013.01); *A61N 1/36025* (2013.01); *A61N 1/37217* (2013.01)

(58) Field of Classification Search
CPC .................................................. A61N 1/0472
See application file for complete search history.

(56) References Cited

U.S. PATENT DOCUMENTS

| | | | |
|---|---|---|---|
| 2009/0088619 A1* | 4/2009 | Turner et al. | 600/383 |
| 2009/0099623 A1 | 4/2009 | Bentwich | |
| 2012/0191000 A1* | 7/2012 | Adachi et al. | 600/544 |
| 2012/0209346 A1* | 8/2012 | Bikson et al. | 607/45 |
| 2013/0245486 A1 | 9/2013 | Simon | |
| 2013/0345774 A1 | 12/2013 | Paulus et al. | |
| 2015/0112403 A1* | 4/2015 | Ruffini et al. | 607/45 |

FOREIGN PATENT DOCUMENTS

| | | |
|---|---|---|
| EP | 2664356 A1 | 11/2013 |
| WO | 2007/138598 A2 | 12/2007 |

(Continued)

OTHER PUBLICATIONS

International Search Report and Written Opinion received for International Patent Application No. PCT/FI2015/050001, dated May 6, 2015, 13 pages.

*Primary Examiner* — Carl H Layno
*Assistant Examiner* — Jennifer Ghand
(74) *Attorney, Agent, or Firm* — Ziegler IP Law Group, LLC

(57) ABSTRACT

A system for transcranial stimulation of a head region of a subject includes an electrode arrangement having a plurality of electrodes coupled to an electrode drive arrangement. The electrodes are operable to contact onto a scalp of the head region of the subject and the drive arrangement is operable to generate electrical signals for driving the plurality of electrodes to cause transcranial stimulation of the head region of the subject. The system further includes a monitoring arrangement for monitoring spatial positions of the plurality of electrodes relative to the head region of the subject, and for indicating positional errors of the electrodes for enabling repositioning of the electrodes and/or a change in the electrical signals applied to the electrodes, for providing improved transcranial stimulation of the head region of the subject and/or mutual relative positions of the plurality of electrodes.

15 Claims, 5 Drawing Sheets

(56) References Cited

FOREIGN PATENT DOCUMENTS

| WO | 2008/015667 | A2 | 2/2008 |
| WO | 2010/120823 | A2 | 10/2010 |
| WO | 2012/059917 | A1 | 5/2012 |
| WO | 2013/032710 | A1 | 3/2013 |
| WO | 2013/192582 | A1 | 12/2013 |

* cited by examiner

SYSTEM AND A METHOD FOR TRANSCRANIAL STIMULATION OF A HEAD REGION OF A SUBJECT

The present disclosure generally relates to transcranial direct current stimulation, and more specifically relates to monitoring transcranial stimulation of a head region of a subject; the present disclosure is, for example, concerned with systems and methods for transcranial stimulation of head regions of subjects. Moreover, aspects of the disclosure are also directed to software products recorded on machine-readable data storage media, wherein such software products are executable upon computing hardware, to implement the aforesaid methods of the disclosure.

BACKGROUND

Transcranial direct current stimulation (tDCS) is a form of neurostimulation which includes, for example, delivering a constant and low current directly to a brain region of a person, namely a subject, through electrodes; such a low current is optionally in a range of 0.5 mA to 2 mA, but is optionally greater than 2 mA, or less than 0.5 mA in certain circumstances. tDCS is useful, for example, for treating patients with brain injuries, such as strokes, for treating depression, anxiety, tinnitus, chronic pain, and for enhancing language and mathematical abilities, addressing attention span problem, for enhancing problem solving abilities, for improving memory, and for enhancing a coordination of body movements.

A known tDCS device includes an anode, a cathode and a battery powered device that is operable to deliver a constant current signal; optionally, the known tDCS device is also susceptible to being mains-powered from an electrical supply network. The anode is a positively charged electrode and the cathode is a negatively charged electrode. During treatment, one of these electrodes is placed over a head region of a person and another electrode is placed at another location, such as a neck region or shoulder region of the person. Once the electrodes are placed correctly, a stimulation procedure may be started. The battery- and/or mains-powered device includes one or more controls for setting the current signal as well as for adjusting a duration of the stimulation procedure. The constant current signal flows from the anode through a skull and brain of the person and thereafter to the cathode, creating an electrical circuit.

Spatial positions of the anode and the cathode on person's head is crucial, as different medical disorders require modulation of different brain regions, and consequently different spatial positions of the anode and cathode on person's head, and a slight variation in a relative spatial distance between the anode and cathode may significantly influence an effectiveness of such treatment. Conventionally, medical professionals, i.e. doctors, manually place the anode and cathode on the person's head in accordance with an internationally recognized '10-20 system', which is a system for describing locations which are appropriate when applying scalp electrodes in a context of an EEG test or experiment. This system is based on a relationship between a location of a given electrode and a corresponding underlying area of cerebral cortex. The "10-20 system" uses locations of cranial landmarks, such as nasion, inion, left and right tragus to determine electrode positions on the scalp. The "10" and "20" refer to the fact that actual distances between adjacent electrodes are either 10% or 20% of the total front-back, namely nasion to inion, or right-left, namely right tragus to left tragus, distance of the skull of the person.

However, the manual placement of electrodes by doctors is susceptible to positional errors, and even a small positional error may affect the overall effectiveness of the treatment. A correct placement of the electrodes is particularly important when the electrodes are used to deliver therapeutic stimulation in repeated stimulation sessions on, for example, consecutive days. In other words, an accurate reproduction of a stimulation site is therefore important. Therefore, there exists a need for a method and system that monitors positions of electrodes on a given head region, or forces the positions based on anatomical markers, that enables the positional errors of electrodes to be reduced, and facilitates repositioning the electrodes for an improved transcranial stimulation.

In a scientific publication "*Transcranial direct current stimulation: State of the art 2008*" (Nitsche et al., Brain Stimulation (200) 1, pp 206-223, Elsevier), positions for placement of electrodes for performing transcranial stimulation are provided, for example as shown in FIG. 1 of this publication. Various issues associated with transcranial direct current stimulation (tDCS) are described, including side effects resulting from electrochemical reactions occurring at positions where associated electrodes are placed on a head region of a given person. Effects experienced by the given person when subject to tDCS are described in the scientific publication, for example in comparison to transcranial magnetic brain stimulation.

SUMMARY

The present disclosure seeks to provide a system for transcranial stimulation of a head region of a subject, and a method of implementing the same.

In one aspect, embodiments of the present disclosure provide a system for transcranial stimulation of a head region of a subject. The system includes an electrode arrangement comprising a plurality of electrodes coupled to at least one electrode drive arrangement. The plurality of electrodes are operable to contact onto a scalp of the head region of the subject and the at least one drive arrangement is operable to generate electrical signals for driving the plurality of electrodes to cause transcranial stimulation of the head region of the subject. The system further includes a monitoring arrangement for monitoring spatial positions of the plurality of electrodes relative to the head region of the subject and/or mutual relative positions of the plurality of electrodes, and for indicating positional errors of the one or more electrodes for enabling repositioning of the plurality of electrodes and/or a change in the electrical signals applied to the plurality of electrodes, for providing improved transcranial stimulation of the head region of the subject.

The electrode arrangement may include features which enable measuring of spatial positions of the plurality of electrodes relative to the head region using a sensing arrangement of the monitoring arrangement, wherein the sensing arrangement is coupled to a computing hardware of the monitoring arrangement for computing the positional errors of the one or more electrodes. According to an embodiment, the computing hardware is operable to access at least one database, for retrieving information for use in computing the positional errors.

The features optionally include one or more light sources which are individually excitable for indicating the spatial positions of their respective electrodes relative to the head region of the subject. The features are susceptible to being imaged using one or more image sensors directed to image the features. The light sources of the features may be implemented as one or more light emitting diodes (LED). Optionally, camera detection of electrodes or cranial landmarks is facilitated by using one or more coloured markers, one or more markers with specific patterns, or any other tool typically used to facilitate computer vision systems. The features may also include figures with a combination of colours. The features may also include both one or more light sources and figures.

The sensing arrangement is optionally implemented, at least in part, using a mobile wireless communication device equipped with at least one imaging sensor for imaging the features for generating at least one image signal for the computing hardware for use in computing the positional errors. The mobile wireless communication device may be implemented using at least one of: a smart phone, a cell phone, a mobile telephone, a wireless-enabled tablet computer, a wireless-enabled phablet computer, a wearable wireless-enabled computer, and a wireless-enabled wrist-worn computer. According to an embodiment, the computing hardware is implemented at least in part remotely from the electrode arrangement, and coupled via a communication network to the sensing arrangement and the drive arrangement.

Optionally, another implementation of the sensing arrangement is achieved using a sensing instrument, for example a small sensing instrument such as a gyroscope, a 3D accelerometer or a combination thereof, attached directly into the stimulating electrode, wherein the sensing instrument is operable to feed positioning data to an external computing device, for example a portable computer, tablet, mobile phone, and so forth. By employing such an arrangement, electrode positions are susceptible to being measured, as well as a corresponding head position needs, for enabling correct positions of the electrodes when administering tDCS or similar.

By sensing the electrode positions with respect to the head, it is possible to use various tools, for example to guide placement of the electrodes, to notify use about the movement of the electrodes, abort a given stimulation when electrodes have moved, and so forth.

According to an embodiment, the system is operable to adjust one or more drive signals generated by the drive arrangement for the plurality of electrodes as a function of the positional errors and/or to provide an indication of repositioning of the electrode arrangement that is required to be performed on the subject to reduce the positional errors.

In another aspect, the present disclosure relates to a method of implementing transcranial stimulation of a head region of a subject, wherein the method includes:
(i) using an electrode arrangement comprising a plurality of electrodes coupled to at least one electrode drive arrangement, wherein the plurality of electrodes are operable to contact onto a scalp of the head region of the subject;
(ii) using the at least one drive arrangement to generate electrical signals for driving the plurality of electrodes to cause transcranial stimulation of the head region of the subject.

The method further includes using a monitoring arrangement for monitoring spatial positions of the plurality of electrodes relative to the head region of the subject and/or mutual relative positions of the plurality of electrodes, and for indicating positional errors of the one or more electrodes for enabling repositioning of the plurality of electrodes and/or a change in the electrical signals applied to the plurality of electrodes, for providing improved transcranial stimulation of the head region of the subject.

In another aspect, embodiments of the present disclosure provide an electrode arrangement for use in the method of implementing the transcranial stimulation of a head region of a subject.

In yet another aspect, embodiments of the present disclosure provide a software product stored on a non-transient machine-readable data storage media, such that the software product is executable upon computing hardware for implementing the method of implementing the transcranial stimulation of a head region of the subject.

Embodiments of the present disclosure provide a system and method for monitoring the spatial positions of electrodes relative to the head region and providing a feedback to the operator accordingly. Based on the feedback, the operator may reposition the electrodes for an improved transcranial stimulation. Alternatively, the system and method may modify/control electrical signals to be applied to the electrodes for the improved transcranial stimulation. The system and method employ a camera to capture images of the electrodes and a monitoring arrangement to compute positional errors based on actual and desired positions of the electrodes; alternatively, or additionally, a 3D tracking instrument attached to the electrodes, or a mechanically-implemented arrangement relying on cranial landmarks can be used for ensuring correct positioning of electrodes.

Additional aspects, advantages, features and objects of the present disclosure would be made apparent from the drawings and the detailed description of the illustrative embodiments construed in conjunction with the appended claims that follow.

It will be appreciated that features of the invention are susceptible to being combined in various combinations without departing from the scope of the invention as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the invention is not limited to specific methods and instrumentalities disclosed herein. Moreover, those in the art will understand that the drawings are not to scale. Wherever possible, like elements have been indicated by identical numbers.

DETAILED DESCRIPTION OF ILLUSTRATIVE EMBODIMENTS

The following detailed description illustrates embodiments of the disclosure and ways in which it can be implemented. Although the best mode of carrying out the invention has been disclosed, those in the art would recognize that other embodiments for carrying out or practicing the invention are also possible.

In overview, a system for transcranial stimulation of a head region of a subject is provided, wherein the system includes an electrode arrangement comprising a plurality of electrodes coupled to at least one electrode drive arrangement, wherein the plurality of electrodes are operable to contact onto skin of the head region of the subject, and wherein the at least one drive arrangement is operable to generate electrical signals for driving the plurality of electrodes to cause transcranial stimulation of the head region of the subject. The system includes a monitoring arrangement for monitoring spatial positions of the plurality of electrodes relative to the head region of the subject, and for indicating positional errors of the one or more electrodes for enabling repositioning of the plurality of electrodes and/or a change in the electrical signals applied to the plurality of electrodes, for providing improved transcranial stimulation of the head region of the subject.

Figure 1:
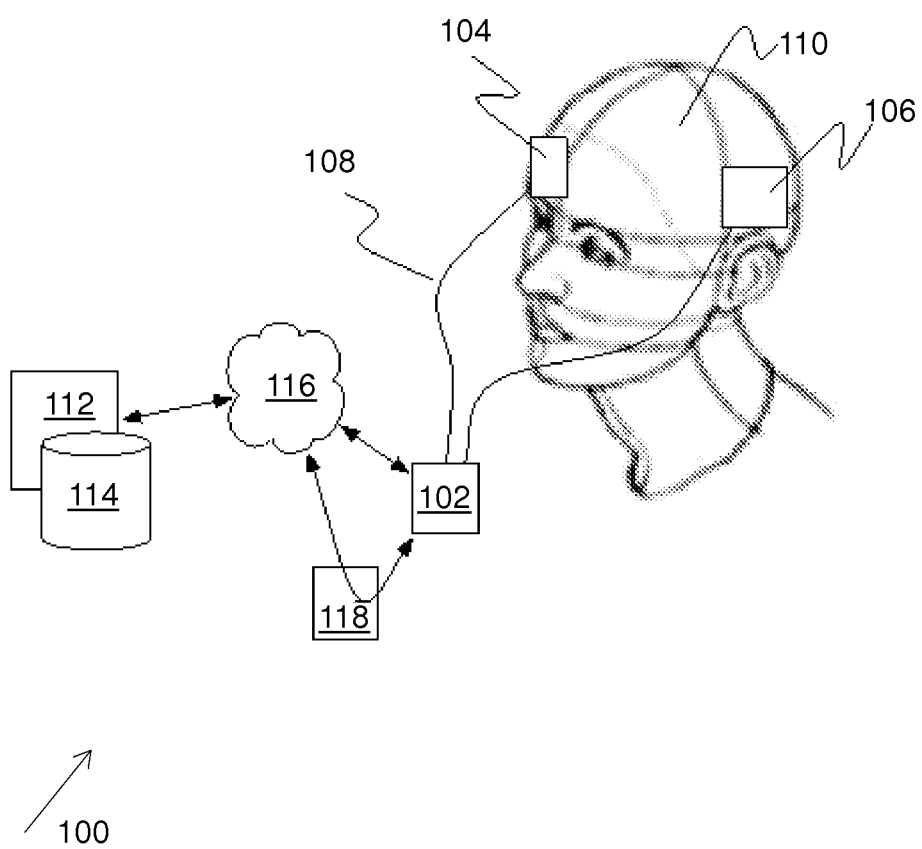
FIG. 1 is an illustration of a system for transcranial stimulation of a head region of a subject, that is suitable for practicing various implementations of the present disclosure.

Referring now to the drawings, particularly by their reference numbers, FIG. 1 is an illustration of a system 100 that is suitable for practicing various implementations of the present disclosure. The system 100 includes a power controller 102 and electrical contacts 104 and 106, where the electrical contacts 104 and 106 are positioned on a head region 110 of a subject, for example a user, and connected to the power controller 102 through wires 108. The electrical contact 104 is a positive electrode, i.e., anode 104, and the electric contact 106 is a negative electrode, i.e. cathode 106. The power controller 102 includes an electrode drive arrangement that generates electric signals for driving the anode 104 and cathode 106 to cause transcranial stimulation of the head region 110 of the subject. In an example, the power controller 102 includes a power source for providing a constant low current to the anode 104, which flows through the skull and brain to the cathode 106, thereby creating a circuit. By "low current" is included currents of 20 milliAmperes (mA) or less, for example usually in an order of microamperes (µA). Optionally, the low current is in a range of 0.1 mA to 4 mA.

The power controller 102 further includes a microcontroller (not shown) connected to the power source for enabling an operator and/or the user to set one or more parameters of transcranial stimulation of the head region 110. In an embodiment, the power controller 102 is operated locally by an operator. In another embodiment, the power controller 102 is operated remotely by a remote operator using an application executing on a remote server system 112, wherein the server system 112 includes a database 114 and is connected to the power controller 102 via a communication network 116. Examples of the communication network 116 include, but are not limited to: Internet, Local Area Network (LAN) and Wide Area Network (WAN). In yet another embodiment, the power controller 102 may be operated locally by an operator using their mobile wireless communication device 118. Examples of the mobile wireless communication device 118, include, but are not limited to, a smart phone, a cell phone, a mobile telephone, a wireless-enabled tablet computer, a wireless-enabled phablet computer, a wearable wireless-enabled computer, and a wireless-enabled wrist-worn computer.

FIG. 1 is merely an example, which should not unduly limit the scope of the claims herein. One of ordinary skill in the art would recognize many variations, alternatives, and modifications of embodiments herein.

Figure 2A:
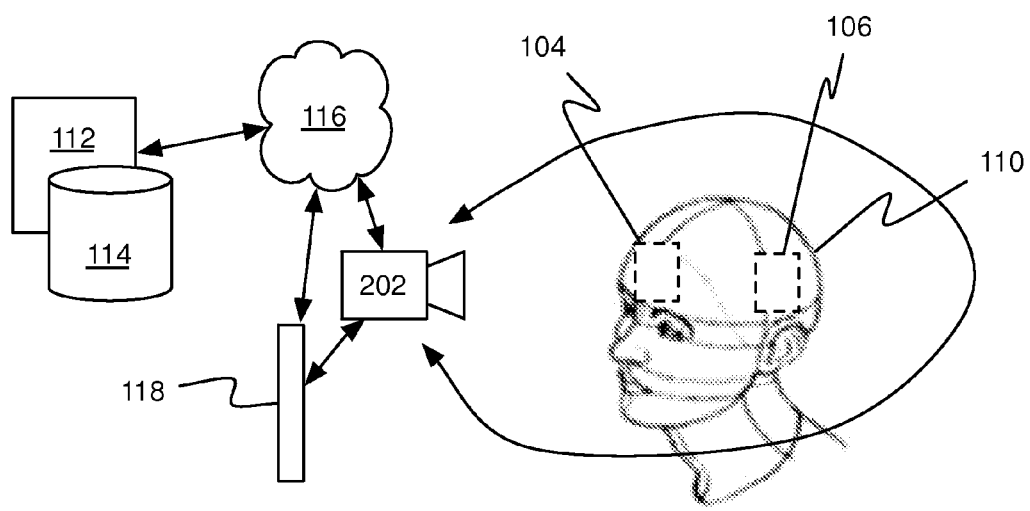
FIGS. 2A and 2B are an illustration of monitoring and improving transcranial stimulation of a head region of a subject, in accordance with the present disclosure.

FIG. 2A is an illustration of a sensing arrangement 202 for the transcranial stimulation of the head region 110, in accordance with the present disclosure. The sensing arrangement 202 includes at least one camera for capturing one or more images of the head region 110 when the anode 104 and cathode 106 are positioned on the head region 110; optionally, the sensing arrangement 202 includes a plurality of cameras for obtaining a 3-D representation of the head region 110, namely to capture a 3-D stereoscopic image of the head region 110. In an embodiment, both the anode 104 and cathode 106 include one or more light sources which are individually excitable for indicating the spatial positions of their respective electrodes relative to the head region 110. In an example, the light sources are optionally implemented as one or more light emitting diodes (LED). Optionally, the light sources are temporally excited in a strobed manner, and the sensing arrangement 202 is operable to detect the light sources by detecting changes in imaged light intensity therefrom when demodulating the image light signals against a corresponding strobe signal, thereby removing influencing effects due to pseudo-constant ambient illumination which is incident upon the head region 110. Optionally, figures or shapes, namely graphical markers, devoid of light emitting diodes (LED) are additionally or alternatively employed for implementing the sensing arrangement 202. Optionally, the sensing arrangement 202 then employs optical pattern-recognition apparatus for detecting spatial locations of the figures or shapes.

The sensing arrangement 202 is optionally either a standalone smart camera or integrated with the mobile wireless communication device 118. For example, when the mobile wireless communication device 118 is a laptop, the camera sensing arrangement 202 is optionally a web-camera and when the device 118 is a smart phone, the sensing arrangement 202 is optionally a mobile camera.

In an embodiment, the sensing arrangement 202 optionally provides the captured images to the mobile wireless communication device 118 for further analysis. In another embodiment, the mobile wireless communication device 118 optionally sends the received images to the server system 112 for further analysis. In yet another embodiment, the sensing arrangement 202 optionally sends the images directly to the server system 112 for further analysis over the communication network 116.

The mobile wireless communication device 118 and/or the server system 112, optionally includes a monitoring arrangement for measuring the spatial positions of the anode 104 and cathode 106 based on the received images, comparing the measured spatial positions with the desired spatial positions, for example spatial positions corresponding to a given desired treatment, computing the positional errors of the anode 104 and cathode 106, if any, and indicating the positional errors to an operator of the system 100. In an embodiment, the monitoring arrangement optionally refers to the database 114 for computing the positional errors, wherein the database 114 optionally includes desired spatial positions of the anode 104 and cathode 106 against one or more types of treatments being implemented. In another embodiment, the monitoring arrangement is optionally a software application executing on the server system 112 and/or the device 118, and providing a user interface on the device 118 for enabling the operator to select a treatment type and view the positional errors.

Figure 2B:
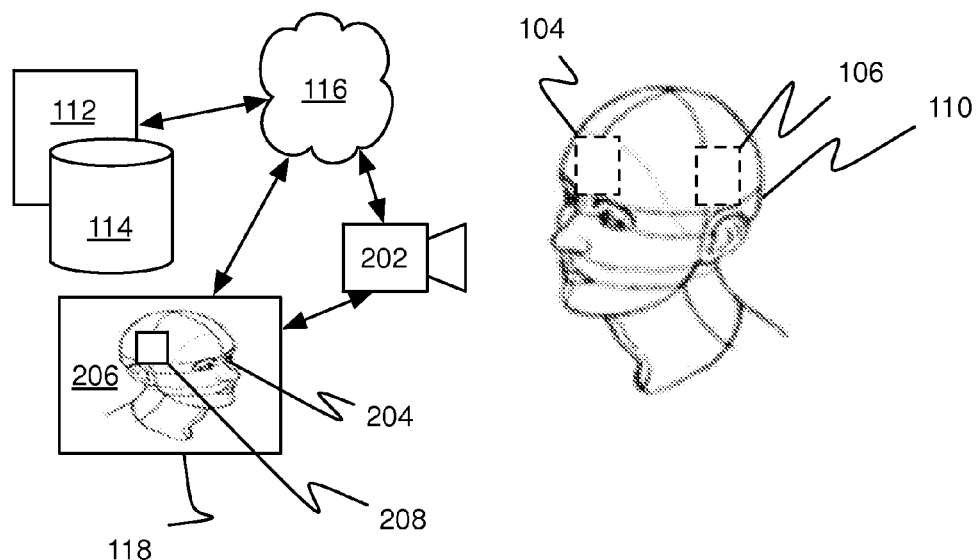

FIG. 2B is an illustration of improving the transcranial stimulation of the head region 110 of the subject, in accordance with the present disclosure. The monitoring arrangement displays a three-dimensional image 204 on a user interface 206 of the mobile wireless communication device 118, wherein the three-dimensional image 204 includes at least one indicator 208 to indicate to the operator whether or not one or more of the current spatial positions of the electrodes 104 and 106 on the head region 110 are correct. The indicator 208 points towards one or more correct positions if the one or more current positions are not correct, thus providing a feedback to the operator. The operator is optionally able to reposition the anode 104 and/or the cathode 106 based on the feedback, and after such repositioning, the sensing arrangement 202 optionally again captures an image and sends it to the device 118 or server 112 for analysis. This process may be iterated until the at least one indicator 208 indicates that the one or more correct positions of the electrodes 104 and 106 have been achieved.

In an embodiment, the monitoring arrangement is optionally coupled to the power controller 102 for controlling current supply to the anode 104 and/or the cathode 106 based on their measured spatial positions relative to the head region 110, optionally also their mutually relative positions. In an example, the monitoring arrangement is operable to enable the power controller 102 to provide electrical signals to the electrodes 104 and 106 only when the positions of the electrodes 104 and 106 have been verified. In another embodiment, the monitoring arrangement is optionally operable to adjust one or more electrical signals generated by the power controller 102 as a function of the positional errors pertaining to placement of the electrodes, for providing improved transcranial stimulation of the head region 110. Optionally, there is employed a positioning system which receives as its measurement parameter patient feedback relating to treatment effectiveness; for example, " . . . an electrode position A yielded a better treatment outcome than an electrode position B, thus please move the electrode to the position A . . . ". Optionally, the sensing arrangement is configured to capture images of the head region 110 before anode 104 or cathode 106 are placed in the head region 110. This way a user interface 264 can indicate to the operator, where the anode 104 and cathode 106 should be placed.

Figure 6:
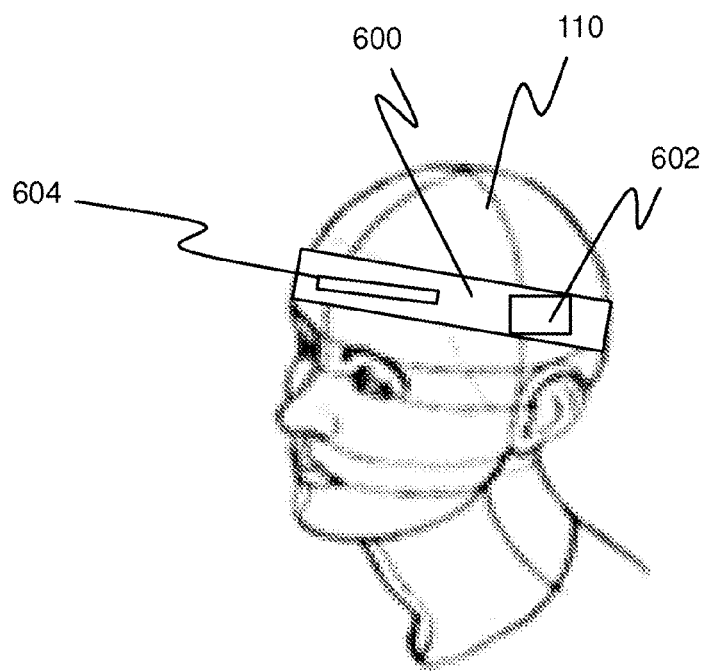
FIG. 6 is an illustration of visual markers in a headband used for transcranical stimulation.

In an exemplary embodiment, the anode 104 and the cathode 106 are optionally positioned on the head region 110 in a form of a head band or a cap, and the monitoring arrangement is then optionally used to position correctly the headband 600. Headband 600 is illustrated in FIG. 6. The headband 600 optionally includes a set of LED's 604 which are optionally illuminated temporally one by one to calibrate a spatial position of the headband on the head region 110. Moreover, the headband optionally has a predefined texture 602 such as figure/barcode/2d bar coder with an associated predefined size. The monitoring arrangement optionally uses at least one predefined texture 602 to determine a size and an orientation of the headband in comparison to a nose and/or an ear associated with the head region 110, and so forth. The texture may provide one or more measurements to determine whether or not the relative position of the headband 600 is in a right place, for example in comparison with an ear lobe or an ear canal of the head region 110.

Figure 3:
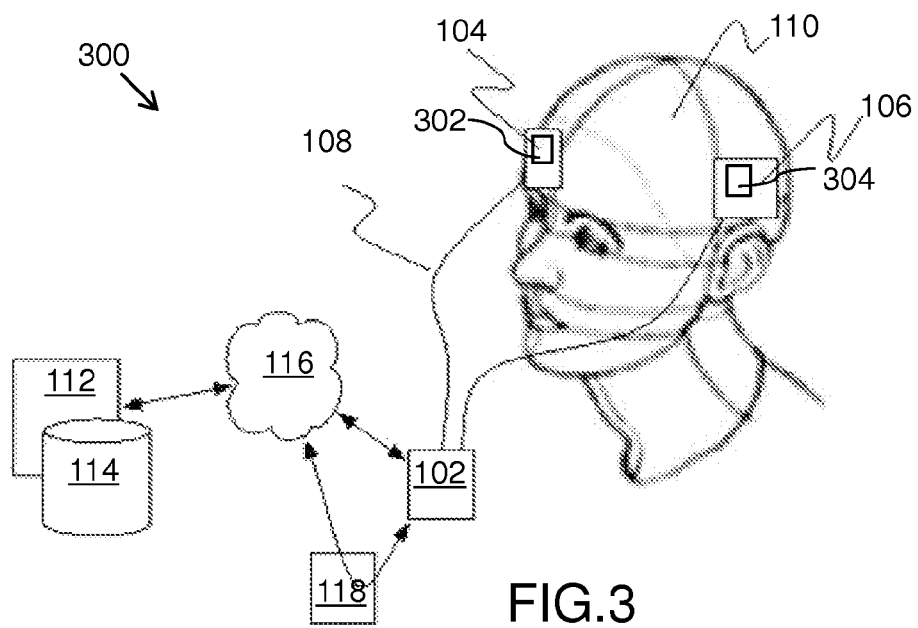
FIG. 3 is an illustration of motion sensors attached to the electronic contacts of the system of FIG. 1, in accordance with the present disclosure.

FIG. 3 is an illustration of motion sensors 302 and 304 attached to the electronic contacts 104 and 106 respectively, in accordance with the present disclosure. The motion sensors 302 and 304 are positioning devices that may be implemented using a gyroscope or a 3D accelerometer or a 3D tracking instrument, or a combination thereof; for example, the gyroscope or the 2D accelerometer are beneficially implemented as micromachined Silicon sensors and/or miniature optical fibre gyroscopes. The motion sensors 302 and 304 are attached directly to the electrodes 104 and 106, and are operable to feed positioning data to an external computing device 118, for example a portable computer, tablet, mobile phone, and so forth. By employing such an arrangement, electrode positions are susceptible to being measured, as well as a corresponding head position needs, for enabling correct positions of the electrodes when administering tDCS or similar.

Figure 4:
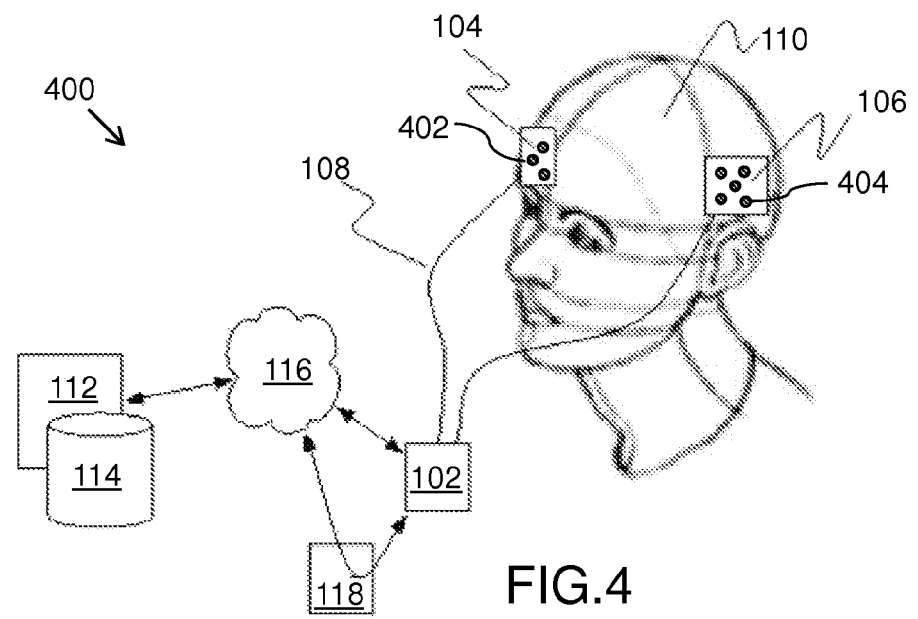
FIG. 4 is an illustration of visible patterned markers on the electronic contacts of the system of FIG. 1, in accordance with the present disclosure.

FIG. 4 is an illustration of visible patterned markers 402 and 404 on the electronic contacts 104 and 106 respectively, in accordance with the present disclosure. The markers 402 and 404 are implemented using one or more coloured markers, or one or more markers with specific patterns, or figures or shapes, namely graphical markers. Optionally, the sensing arrangement 202 then employs optical pattern-recognition apparatus for detecting spatial locations of the visible patterned markers 402 and 404 for detecting spatial positions of the electrodes 104 and 106.

Figure 5:
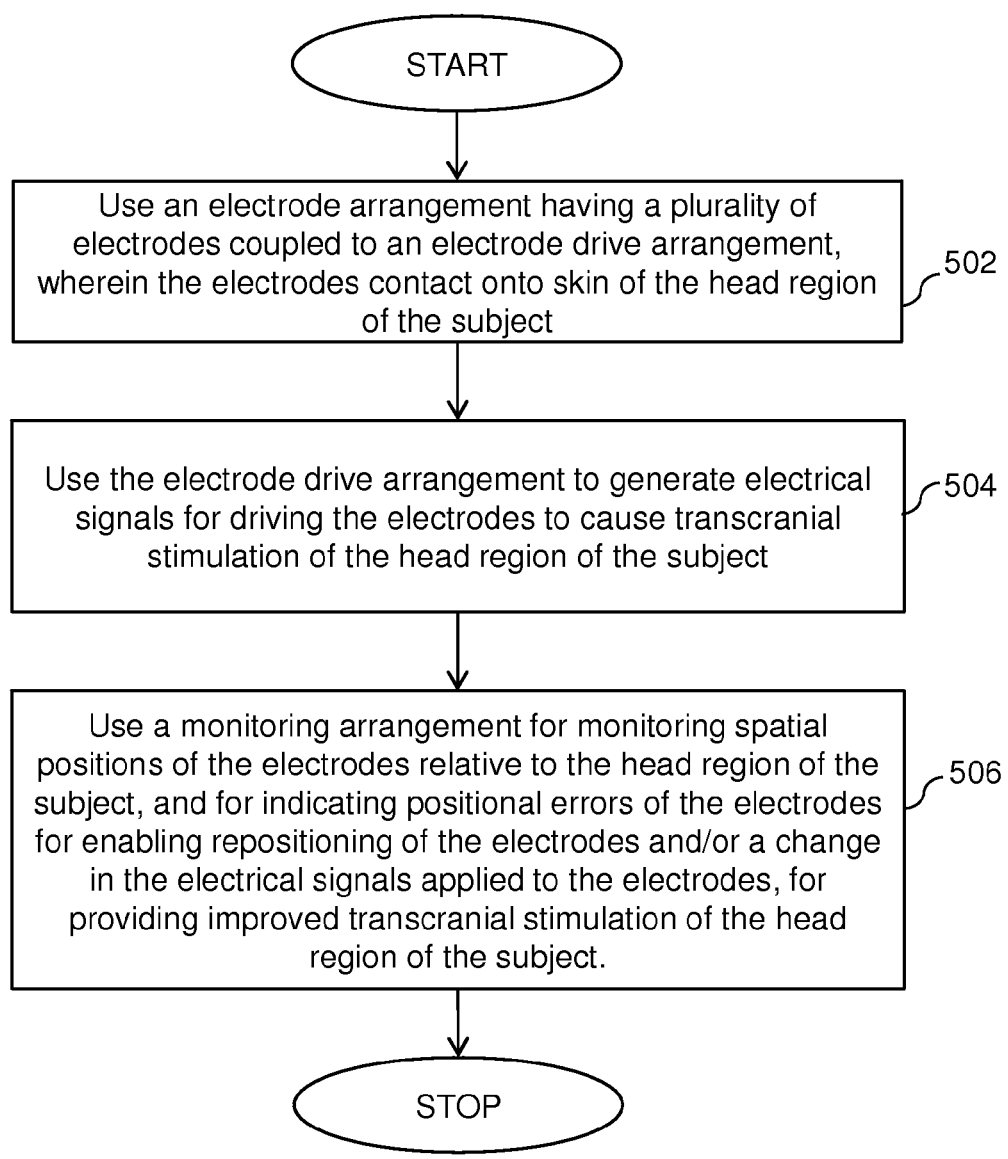
FIG. 5 is an illustration of steps of a method of implementing transcranial stimulation of a head region of a subject, in accordance with the present disclosure.

FIG. 5 is an illustration of steps of a method of implementing transcranial stimulation of the head region 110, in accordance with the present disclosure; it will be appreciated that such transcranial stimulation is not limited to methods of treatment of the animal or human body, but can be for other purposes also, for example for relieving stress, for relaxation, for comfort and so forth. The method is depicted as a collection of steps in a logical flow diagram, which represents a sequence of steps that can be implemented in hardware, software, or a combination thereof.

At a step 502, an electrode arrangement having a plurality of electrodes 104 and 106 coupled to an electrode drive arrangement is used for transcranial stimulation of the head region 110, wherein the electrodes 104 and 106 contact onto skin of the head region 110 of the subject.

At a step 504, the electrode drive arrangement is used to generate electrical signals for driving the electrodes 104 and 106 to cause transcranial stimulation of the head region 110 of the subject.

At a step 506, a monitoring arrangement is used that monitors spatial positions of the electrodes 104 and 106 relative to the head region 110 of the subject and indicates positional errors of the electrodes 104 and 106 for enabling their repositioning and/or a change in the electrical signals applied to the electrodes 104 and 106 for providing improved transcranial stimulation of the head region 110.

It should be noted here that the steps 502 to 506 are only illustrative and other alternatives can also be provided where one or more steps are added, one or more steps are removed, or one or more steps are provided in a different sequence without departing from the scope of the claims herein.

FIG. 5 is merely an example, which should not unduly limit the scope of the claims herein. One of ordinary skill in the art would recognize many variations, alternatives, and modifications of embodiments herein.

According to further embodiments, spatial position of electrodes 104 and 106 can be determined by combination of visual tracking, for example as shown in FIG. 2A, FIG. 2B and/or FIG. 4, and positioning devices, for example as shown in FIG. 3. As an example, visual tracking is optionally used to determine one or more reference points on a head as a location for the first electrode. 104 The first electrode 104 is optionally one that is positioned in a forehead region when in use. The second electrode 106 is then positioned using an accelerometer/ultrasound, or other distance, velocity or acceleration measuring means, in respect to the first electrode 104.

Although embodiments of the present invention have been described comprehensively in the foregoing, in considerable detail to elucidate the possible aspects, those skilled in the art would recognize that other versions of the invention are also possible.

We claim:

1. A system for transcranial stimulation of a head region of a subject, comprising:

an electrode arrangement comprising a plurality of electrodes coupled to at least one electrode drive arrangement, wherein the plurality of electrodes are operable to contact onto a scalp of the head region of the subject, wherein the at least one drive arrangement is operable to generate electrical signals for driving the plurality of electrodes to cause transcranial stimulation of the head region of the subject; and a monitoring arrangement configured for monitoring spatial positions of the plurality of electrodes relative to one or more of the head region of the subject or mutual relative positions of the plurality of electrodes, and for indicating positional errors of the one or more of the plurality of electrodes for enabling one or more of a repositioning of the plurality of electrodes or a change in the electrical signals applied to the plurality of electrodes, for providing improved transcranial stimulation of the head region of the subject, wherein the electrode arrangement includes features which enable spatial positions of the plurality of electrodes relative to the head region to be measured using a sensing arrangement of the monitoring arrangement, wherein the sensing arrangement is coupled to computing hardware of the monitoring arrangement for computing the positional errors of the one or more electrodes.

2. The system as claimed in claim 1, wherein the sensing arrangement is implemented, at least in part, using a mobile wireless communication device equipped with at least one imaging sensor for imaging the features for generating at least one image signal for the computing hardware for use in computing the positional errors.

3. The system as claimed in claim 1, wherein the computing hardware is implemented at least in part remotely from the electrode arrangement, and coupled via a communication network to the sensing arrangement and the drive arrangement.

4. The system as claimed in claim 2, wherein the mobile wireless communication device is implemented using at least one of: a smart phone, a cell phone, a mobile telephone, a wireless-enabled tablet computer, a wireless-enabled phablet computer, a wearable wireless-enabled computer, a wireless-enabled wrist-worn computer.

5. The system as claimed in claim 1, wherein the features include at least one of:

one or more light sources which are individually excitable for indicating the spatial positions of their respective electrodes relative to the head region of the subject; and figures with a combination of colours.

6. The system as claimed in claim 1, wherein the system is operable to adjust one or more drive signals generated by the drive arrangement for the plurality of electrodes as a function of the positional errors and to provide an indication of repositioning of the electrode arrangement that is required to be performed on the subject to reduce the positional errors.

7. The system as claimed in claim 1, wherein the computing hardware is operable to access at least one database, for retrieving information for use in computing the positional errors.

8. A method of implementing transcranial stimulation of a head region of a subject, wherein the method includes:

using an electrode arrangement comprising a plurality of electrodes coupled to at least one electrode drive arrangement, wherein the plurality of electrodes are operable to contact onto a scalp of the head region of the subject;

using the at least one drive arrangement to generate electrical signals for driving the plurality of electrodes to cause transcranial stimulation of the head region of the subject;

using a monitoring arrangement for monitoring spatial positions of the plurality of electrodes relative to one or more of the head region of the subject or mutual relative positions of the plurality of electrodes, and for indicating positional errors of one or more of the plurality of electrodes for enabling one or more of a repositioning of the plurality of electrodes or a change in the electrical signals applied to the plurality of electrodes, for providing improved transcranial stimulation of the head region of the subject; and employing features of the electrode arrangement for enabling spatial positions of the plurality of electrodes relative to the head region to be measured using a sensing arrangement of the monitoring arrangement, wherein the sensing arrangement is coupled to computing hardware of the monitoring arrangement for computing the positional errors of the one or more electrodes.

9. The method as claimed in claim 8, wherein the method includes implementing the sensing arrangement, at least in part, using a mobile wireless communication device equipped with the at least one imaging sensor for imaging the features for generating the at least one image signal for the computing hardware for use in computing the positional errors.

10. The method as claimed in claim 8, wherein the method includes implementing the computing hardware at least in part remotely from the electrode arrangement, and coupled via a communication network to the sensing arrangement and the drive arrangement.

11. The method as claimed in claim 10, wherein the method includes implementing the mobile wireless communication device using at least one of: a smart phone, a cell phone, a mobile telephone, a wireless-enabled tablet computer, a wireless-enabled phablet computer, a wearable wireless-enabled computer, a wireless-enabled wrist-worn computer.

12. The method as claimed in claim 8, wherein the method includes arranging for the features to include one or more light sources which are individually excitable for indicating one or more of the spatial positions of their respective electrodes relative to the head region of the subject or a mutual relative position of the plurality of electrodes.

13. The method as claimed in claim 8, wherein the method includes adjusting one or more drive signals generated by the drive arrangement for the plurality of electrodes as a function of the positional errors and to provide an indication of repositioning of the electrode arrangement that is required to be performed on the subject to reduce the positional errors.

14. The method as claimed in claim 8, wherein the method includes operating the computing hardware to access at least one database, for retrieving information for use in computing the positional errors.

15. A software product stored on non-transient machine-readable data storage media, wherein the software product is executable upon computing hardware for implementing a method as claimed in claim 8.

* * * * *